United States Patent [19]

Nickolson et al.

[11] Patent Number: 5,190,973
[45] Date of Patent: Mar. 2, 1993

[54] 20-ALKYL-7-OXOPROSTACYCLIN DERIVATIVES USEFUL AS PHARMACEUTICALS

[75] Inventors: Robert Nickolson, Berlin; Helmut Vorbrueggen; Claus S. Stuerzebecher; Martin Haberey, all of Berlin, Fed. Rep. of Germany

[73] Assignee: Schering Aktiengesellschaft, Berlin and Bergkamen, Fed. Rep. of Germany

[21] Appl. No.: 599,916

[22] Filed: Oct. 19, 1990

Related U.S. Application Data

[63] Continuation of Ser. No. 277,825, Nov. 30, 1988, abandoned, which is a continuation of Ser. No. 144,139, Jan. 15, 1988, abandoned, which is a continuation of Ser. No. 37,892, Apr. 13, 1987, abandoned, which is a continuation of Ser. No. 917,444, Oct. 10, 1986, abandoned, which is a continuation of Ser. No. 759,039, Jul. 10, 1985, abandoned.

[30] Foreign Application Priority Data

Nov. 10, 1983 [DE] Fed. Rep. of Germany ....... 3340988

[51] Int. Cl.$^5$ .................. A61K 31/34; A61K 31/557; C07D 307/937
[52] U.S. Cl. ..................................... 514/470; 549/465
[58] Field of Search ........................ 549/465; 514/470

[56] References Cited

U.S. PATENT DOCUMENTS

4,364,950 12/1982 Shuballa et al. ............... 549/465
4,466,969 8/1984 Nicholson et al. .............. 549/465

OTHER PUBLICATIONS van Dorp et al., Prostaglandins, vol. 16(6), pp. 953-956.

Primary Examiner—Bernard Dentz
Attorney, Agent, or Firm—Millen, White, Zelano and Branigan

[57] ABSTRACT

The invention concerns 20-alkyl-7-oxoprostacyclin derivatives of general Formula I

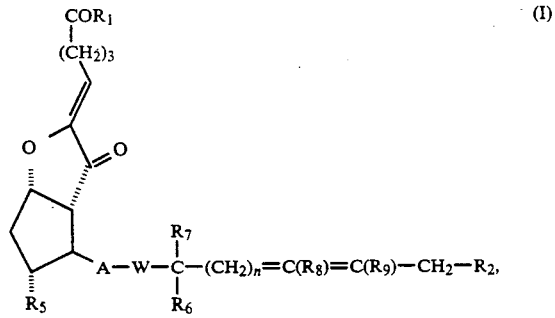

wherein
$R_1$ is the residue $OR_3$ where $R_3$ means hydrogen or alkyl of 1-10 carbon atoms optionally substituted by halogen, phenyl, $C_1$-$C_4$-alkoxy or $C_1$-$C_4$-dialkylamino; cycloalkyl, aryl or a heterocyclic residue, or the residue $NHR_4$ where $R_4$ means hydrogen or an alkanoyl or alkanesulfonyl residue of respectively 1-10 carbon atoms,
n is 1 or 2,
A is a $CH_2$—$CH_2$—, cis—CH=CH— or trans—CH=CH—group,
W is a

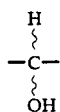

or a

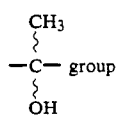

group wherein the OH-group can respectively be esterified with a benzoyl or alkanoic acid residue of 1-4 carbon atoms, or etherified with a tetrahydropyranol, tetrahydrofuranyl, alkoxyalkyl or trialkylsilyl residue, wherein the free or esterified OH-group can be in the α- or β-position,
$R_2$ is a straight-chain or branched-chain alkyl group of 1-6 carbon atoms,
$R_5$ is a hydroxy group which can be esterified with an alkanoic acid residue of 1-4 carbon atoms or etherified with a tetrahydropyranyl, tetrahydrofuranyl, alkoxyalkyl or trialkylsilyl residue,
$R_6$ and $R_7$ are hydrogen or a straight-chain or branched-chain alkyl group of 1-4 carbon atoms, or $R_6$ and $R_7$ jointly represent a trimethylene group,
$R_8$ and $R_9$ jointly represent a linkage or hydrogen or a straight-chain or branched-chain alkyl group of 1-4 carbon atoms,
and, if $R_3$ is hydrogen, the salts thereof with physiologically compatible bases; their production; and their use as medicinal agents.

5 Claims, No Drawings

20-ALKYL-7-OXOPROSTACYCLIN DERIVATIVES USEFUL AS PHARMACEUTICALS

This is a continuation of application Ser. No. 07/277,825, filed Nov. 30, 1988, which is a continuation of Ser. No. 07/144,139, filed Jan. 15, 1988, which is a continuation of Ser. No. 07/037,892, filed Apr. 13, 1987, which is a continuation of Ser. No. 06/917,444, filed Oct. 10, 1986, which is a continuation of Ser. No. 06/759,039, filed Jul. 10, 1985, all now abandoned.

The invention relates to novel prostacyclin derivatives, processes for their production, as well as their use as medicinal agents.

Prostacyclin ($PGI_2$), one of the primary factors in blood platelet aggregation, has a dilating effect on various blood vessels (Science 196 : 1072) and thus could be considered as an agent for lowering blood pressure. However, $PGI_2$ does not possess the stability required for a medicinal agent. Thus, its half-life value at physiological pH values and at room temperature is only a few minutes.

DOS 3,035,454 describes chemically stable and biologically effective 7-oxoprostacyclins.

It has been found that introduction of an alkyl group in the 20-position of the prostacyclin leads to a further rise in efficacy of the 7-oxoprostacyclins, the pharmacological spectrum of effectiveness being preserved, and the duration of activity of the novel prostacyclins being markedly prolonged.

The compounds of this invention inhibit thrombocyte aggregation and have hypotensive and bronchodilatory effects. They furthermore exert cytoprotective action on the heart, liver, stomach, and kidneys and inhibit gastric acid secretion.

The invention concerns 7-oxoprostacyclins of general Formula I

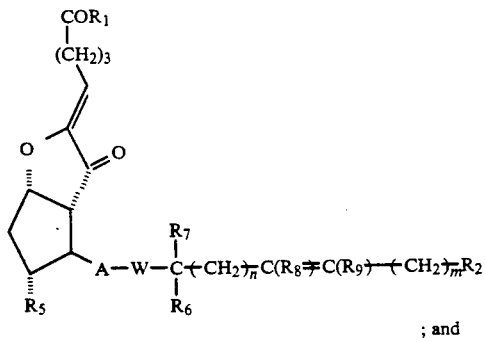

wherein
$R_1$ is the residue $OR_3$ where $R_3$ means hydrogen or alkyl of 1-10 carbon atoms optionally substituted by halogen, phenyl, $C_1$-$C_4$-alkoxy or $C_1$-$C_4$-dialkylamino; cycloalkyl, aryl or a heterocyclic residue, or the residue $NHR_4$ where $R_4$ means hydrogen or an alkanoyl or alkanesulfonyl residue of respectively 1-10 carbon atoms, n is 1 or 2, A is a $CH_2$—$CH_2$—, cis-CH=CH— or trans-CH=CH-group, m is 0 when n is 2;
m is 1 when n is 1;
W is a

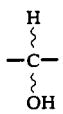

or a

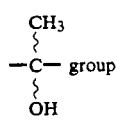 group wherein the OH-group can respectively be esterified with a benzoyl or alkanoic acid residue of 1-4 carbon atoms, or etherified with a tetrahydropyranyl, tetrahydrofuranyl, alkoxyalkyl or trialkylsilyl residue, wherein the free or esterified OH-group can be in the α- or β-position, $R_2$ is a straight-chain or branched-chain alkyl group of 1-6 carbon atoms, $R_5$ is a hydroxy group which can be esterified with an alkanoic acid residue of 1-4 carbon atoms or etherified with a tetrahydropyranyl, tetrahydrofuranyl, alkoxyalkyl or trialkylsilyl residue, $R_6$ and $R_7$ are hydrogen or a straight-chain or branched-chain alkyl group of 1-4 carbon atoms, or $R_6$ and $R_7$ jointly represent a trimethylene group, $R_8$ and $R_9$ jointly represent a linkage or hydrogen or a straight-chain or branched-chain alkyl group of 1-4 carbon atoms, and, if $R_3$ is hydrogen, the salts thereof with physiologically compatible bases.

The alkyl group $R_3$ can be linear or branched alkyl groups of 1-10 carbon atoms, such as, for example, methyl, ethyl, propyl, butyl, isobutyl, tert-butyl, pentyl, neopentyl, heptyl, hexyl, decyl. The alkyl groups $R_3$ can optionally be mono- to polysubstituted by halogen atoms, alkoxy groups of 1-4 carbon atoms, optionally substituted aryl groups, dialkylamines and trialkylammonium of 1-4 carbon atoms. Those alkyl groups are preferred which are monosubstituted. Examples for substituents are fluorine, chlorine or bromine atoms, phenyl, dimethylamine, methoxy, ethoxy. Preferred alkyl groups $R_3$ are those of 1-4 carbon atoms, e.g. methyl, ethyl, propyl, dimethylaminopropyl, isobutyl and butyl.

Aryl groups $R_3$ can be substituted as well as unsubstituted aryl groups, such as, for example, phenyl, 1-naphthyl and 2-naphthyl, each of which can be substituted by 1-3 halogen atoms, a phenyl group, 1-3 alkyl groups of respectively 1-4 carbon atoms, a chloromethyl, fluoromethyl, trifluoromethyl, carboxy, hydroxy or alkoxy group of 1-4 carbon atoms. Preferred are the substituents in the 3- and 4-positions on the phenyl ring, for example by fluorine, chlorine, alkoxy or trifluoromethyl or in the 4-position by hydroxy.

The cycloalkyl group $R_3$ can contain in the ring 4-10, preferably 5 and 6 carbon atoms. The rings can be substituted by alkyl groups of 1-4 carbon atoms. Examples worth citing are cyclopentyl, cyclohexyl, methylcyclohexyl and adamantyl.

Suitable heterocyclic groups $R_3$ are 5- and 6membered heterocycles; among them, those with a hetero atom, such as, for example, nitrogen, oxygen or sulfur, are especially preferred. Examples are: 2-furyl, 2-thienyl, 2-pyridyl, 3-pyridyl, 4-pyridyl, and others.

Suitable as the acid residue $R_4$ are physiologically compatible acid residues. Preferred acids are organic carboxylic acids and sulfonic acids of 1-15 carbon atoms pertaining to the aliphatic, cycloaliphatic, aromatic, aromatic-aliphatic and heterocyclic series. These acids can be saturated, unsaturated and/or polybasic and/or conventionally substituted. Examples for substituents that can be mentioned are alkyl, hydroxy, alkoxy, oxo or amino groups, or halogen atoms.

The following carboxylic acids are recited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di-, and trichloroacetic acids, aminoacetic acid, diethylaminoacetic acid, piperidinoacetic acid, morpholinoacetic acid, lactic acid, succinic acid, adipic acid, benzoic acid, benzoic acids substituted by halogen, trifluormethyl, hydroxy, alkoxy, or carboxy groups, nicotinic acid, isonicotinic acid, furan-2-carboxylic acid, cyclopentylpropionic acid. Especially preferred acyl residues are considered to be those of up to 10 carbon atoms. Examples for sulfonic acids are methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acids.

The hydroxy groups $R_5$ and those in W can be functionally modified, for example by etherification or esterification, wherein the free or modified hydroxy groups in W can be in the α- or β-position, free hydroxy groups being preferred. Suitable ether and acyl residues are those known to persons skilled in the art. Ether residues that can be easily split off are preferred, e.g. the tetrahydropyranyl, tetrahydrofuranyl, α-ethoxyethyl, trimethylsilyl, dimethyl-tertbutylsilyl and tribenzylsilyl residues. Acyl residues can be $C_1$-$C_4$-alkanoyl residues, such as, for example, acetyl, propionyl, butyryl or benzoyl.

Suitable alkyl groups $R_2$ are straight-chain and branched-chain alkyl residues of 1-6 carbon atoms. Examples are methyl, ethyl, propyl, butyl, isobutyl, tert-butyl, pentyl, hexyl. Among the alkyl residues $R_2$, those of 1-4 carbon atoms are especially preferred.

Suitable alkyl groups $R_6$, $R_7$, $R_8$ and $R_9$ are straight-chain or branched-chain alkyl residues of 1-4 carbon atoms, as recited for $R_2$ above.

Inorganic and organic bases, as they are known to a person skilled in the art for the formation of physiologically compatible salts, are suitable for salt formation with the free acids ($R_3$=H).

Examples worth citing are: alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The invention furthermore relates to a process for the preparation of the 7-oxoprostacyclins of this invention according to general Formula I, characterized by conventionally oxidizing a compound of general Formula II

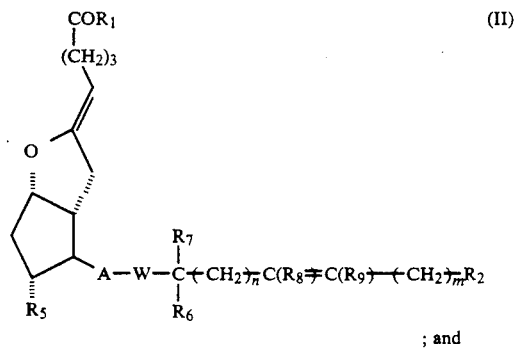

; and wherein n, m, $R_1$, $R_2$, $R_5$, $R_6$, $R_7$, $R_8$, $R_9$, A and W have the meanings given above, with selenium dioxide.

The reaction of the compound of general Formula II with selenium dioxide is performed at temperatures of 20°-140° C., preferably 50°-120° C., in an organic solvent, preferably dioxane or tert-butanol, in 0.5-10 hours under an inert gas (such as, for example, $N_2$ or Ar) and under agitation, optionally with the addition of an amine base, such as pyridine or hexamethyldisilazane.

Saponification of the 7-oxoprostacyclin esters is effected according to methods known to those skilled in the art, for example with alkaline catalysts. Introduction of the ester group wherein $R_3$ is an alkyl group of 1-10 carbon atoms takes place by using methods known to a person skilled in the art. The carboxy compounds are conventionally reacted, for example, with diazohydrocarbons. Esterification with diazohydrocarbons takes place, for example, by mixing a solution of the diazohydrocarbon in an inert solvent, preferably in diethyl ether, with the carboxy compound in the same or in another inert solvent, e.g. methylene chloride. After the reaction is finished within 1-30 minutes, the solvent is removed and the ester purified as usual. Diazoalkanes are either known or can be prepared according to conventional methods [Org. Reactions 8:389-394 (1954)].

Introduction of the ester group $OR_3$ for $R_1$ wherein $R_3$ is a substituted or unsubstituted aryl group takes place with the use of methods known to those skilled in the art. For example, the carboxy compounds are reacted with the corresponding arylhydroxy compounds with dicyclohexylcarbodiimide in the presence of a suitable base, e.g. pyridine or triethylamine, in an inert solvent. Suitable solvents are methylene chloride, ethylene chloride, chloroform, ethyl acetate, tetrahydrofuran, preferably chloroform. The reaction is performed at temperatures of between −30° C. and +50° C., preferably at +10° C.

The 7-oxoprostacyclin derivatives of general Formula I wherein $R_3$ means a hydrogen atom can be converted into salts with suitable amounts of the corresponding inorganic bases, under neutralization. For example, when dissolving the corresponding PG acids in water containing the stoichiometric amount of the base, the solid inorganic salt is obtained after removing the water by evaporation or after addition of a water-miscible solvent, e.g. alcohol or acetone.

In order to produce an amine salt, which process is carried out in the usual way, the prostacyclin acid is dissolved, for example, in a suitable solvent, e.g. ethanol, acetone, acetonitrile, diethyl ether or benzene, and at least the stoichiometric quantity of the amine is added to this solution. During this step, the salt is ordinarily obtained in the solid form, or it is isolated in the usual way after evaporation of the solvent.

The functional modification of the free OH-groups takes place according to methods known to a person skilled in the art. In order to introduce the ether blocking groups, the reaction is conducted, for example, with dihydropyran in methylene chloride, benzene or chloroform with the use of an acidic catalyst, e.g. $POCl_3$, p-toluenesulfonic acid or anhydrous mineral acids. Dihydropyran is used in excess, preferably in two to ten times the amount required theoretically. The reaction is normally completed at 0° C. to 30° C. after 15–30 minutes.

The acyl blocking groups are introduced by conventionally reacting a compound of general Formula I with a carboxylic acid derivative, such as, for example, an acid chloride, acid anhydride, and others, in the presence of a tertiary amine base, such as, for example, pyridine, dimethylaminopyridine, etc.

The liberation of a functionally modified OH-group to obtain the compounds of general Formula I takes place by methods known per se. For example, ether blocking groups are split off in an aqueous solution of an organic acid, such as, for example, acetic acid, propionic acid, etc., or in an aqueous solution of an inorganic acid, e.g. hydrochloric acid. In order to improve solubility, a watermiscible, inert organic solvent is suitably added. Suitable organic solvents are, for example, alcohols, such as methanol and ethanol, and ethers, such as dimethoxyethane, dioxane, and tetrahydrofuran. Tetrahydrofuran is preferably employed. The splitting-off step is conducted preferably at temperatures of between 20° and 80° C.

The silyl ether blocking groups are split off, for example, with tetrabutylammonium fluoride or with KF in the presence of a crown ether. Suitable solvents are, for example, tetrahydrofuran, diethyl ether, dioxane, methylene chloride, etc. The splitting-off step is performed preferably at temperatures of between 0° and 80° C.

The acyl groups are saponified, for example, with alkali or alkaline earth carbonates or hydroxides in an alcohol or in the aqueous solution of an alcohol. Suitable alcohols are aliphatic alcohols, e.g. methanol, ethanol, butanol, etc., preferably methanol. Alkali carbonates and hydroxides that can be mentioned are potassium and sodium salts, but the potassium salts are preferred. Suitable alkaline earth carbonates and hydroxides are, for example, calcium carbonate, calcium hydroxide, and barium carbonate. The reaction takes place at −10° to 70° C., preferably at 25° C.

The reaction of the compound of general Formula I with $R_3$ meaning a hydrogen atom, with an isocyanate of the general formula wherein $R_4$ has the above meanings $$R_4-N=C=O \quad (V)$$

takes place optionally with the addition of a tertiary amine, such as, for example, triethylamine or pyridine. The reaction can be performed without a solvent or in an inert solvent, preferably acetonitrile, tetrahydrofuran, acetone, dimethylacetamide, methylene chloride, diethyl ether, benzene, toluene, dimethyl sulfoxide, at temperatures of below room temperature, e.g. between −80° C. and 100° C., preferably at 0° to 30° C.

The compounds of general Formula II, serving as the starting material, can be prepared, for example, by conventionally reacting a known prostaglandin F derivative of general Formula III

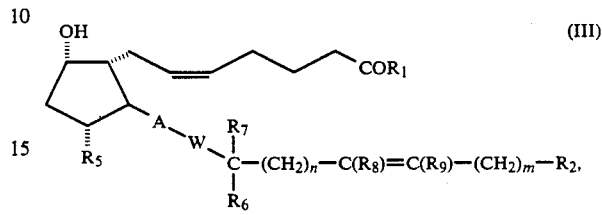

with iodine in the presence of an alkali hydrogen carbonate or alkali carbonate to obtain the compounds of general Formula IV

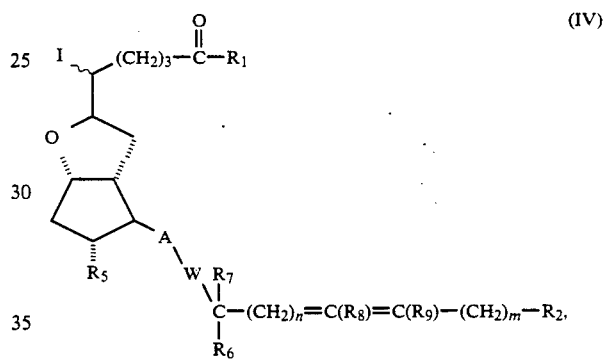

Subsequently, any free hydroxy groups can be blocked by esterification, etherification or silylation. Depending on the desired meaning of A or other residues in the final products of general Formula I, it is possible optionally to hydrogenate double bonds in IV or, if desired, esterify a carboxy group or react a carboxy group with compounds of general Formula V.

The reaction of the compounds of general Formula IV to the compounds of general Formula II can take place, for example, with 1,5-diazabicyclo[3.4.0]nonene-5 (DBN) or 1,5-diazabicyclo[5.4.0]undecene-5 (DBU) in an inert solvent, such as benzene, toluene, tetrahydrofuran, etc., or with sodium methylate in methanol. The splitting off of hydrogen halide is effected at temperatures of between 0° and 120° C., preferably at 20°–60° C.

If, in the final analysis, end products are desired which contain free hydroxy groups in the prostane residue, starting products are suitably employed wherein these are blocked intermediarily by preferably easily cleavable ether or acyl residues.

The compounds of this invention have bloodpressure-lowering and bronchodilatory effects. They are furthermore suitable for inhibiting thrombocyte aggregation. Consequently, the novel prostacyclin derivatives of Formula I represent valuable pharmaceutically active agents. Moreover, with a similar spectrum of activity, they exhibit, a compared with corresponding prostaglandins, higher specificity and, above all, substantially longer efficacy. As compared with $PGI_2$, they are distinguished by higher stability. The high tissue specificity of the novel prostaglandins is demonstrated in a study on smooth-muscle organs, such as, for example, on the guinea pig ileum or on the isolated rabbit trachea, where a substantially lower stimulation can be observed than in the administration of natural prostaglandins of the E-, A- or F-type.

The novel prostaglandin analogs exhibit the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; treatment for stroke, prophylaxis and therapy of coronary heart disease, coronary thrombosis, cardiac infarction, peripheral arterial diseases, arteriosclerosis and thrombosis, therapy for shock, inhibition of bronchoconstriction, inhibition of gastric acid secretion, and cytoprotection for gastric and intestinal mucosa; antiallergic properties, lowering of pulmonary vascular resistance and pulmonary blood pressure, promotion of kidney blood flow, utilization in place of heparin or as adjuvant in dialysis of hemofiltration, preservation of blood plasma stores, especially blood platelet stores, inhibition of labor, treatment of gestational toxicosis, enhancement of cerebral blood flow, etc. Besides, the novel prostaglandin analogues exhibit antiproliferative properties.

The dosage of the compounds is 1-1,500 μg/kg/day if administered to human patients. The unit dosage for the pharmaceutically acceptable carrier is 0.01-100 mg.

Upon intravenous injection administered to nonanesthetized, hypertonic rats in doses of 5, 20 and 100 μg/kg body weight, the compounds of this invention exhibit a stronger blood-pressure-lowering effect and a more prolonged duration of efficacy than $PGE_2$ and $PGA_2$ without triggering diarrhea, as does $PGE_2$, or cardiac arrhythmias, as does $PGA_2$.

Upon intravenous injection administered to anesthetized rabbits, the compounds of this invention show, as compared with $PGE_2$ and $PGA_2$, a stronger and also considerably prolonged blood-pressure-lowering effect without affecting other smooth-muscle organs or organ functions.

Sterile, injectable, aqueous or oily solutions are used for parenteral administration. Suitable for oral administration are, for example, tablets, dragees or capsules. For topical application, suitable are ointments, creams, gels and solutions.

Consequently, the invention also concerns medicinal agents based on the compounds of general Formula I and conventional auxiliary agents and excipients.

The active agents of this invention are to serve, in conjunction with the auxiliary agents known and customary in galenic pharmacy, for example for the preparation of hypotensors.

EXAMPLE 1

16,20-Dimethyl-7-oxo-18,18,19,19-tetradehydro-$PGI_2$ 1a) (1S,5R,6R,7R)-6-[(E)-(4RS)-3-Oxo-4-methylnon-1-en-6-ynyl]-7-benzoyloxy-2-oxabicyclo-[3.3.0]octan-3-one A solution of 6.84 g of dimethyl-(2-oxo-3-methyloct-5-ynyl)phosphonate in 50 ml of anhydrous dimethoxyethane is added dropwise to a suspension of 1.21 g of sodium hydride/oil suspension (55% strength) in 60 ml of dimethoxyethane at room temperature. Thereafter the mixture is stirred for 30 minutes at room temperature and then cooled to −30°. At this point in time, a solution of 6.93 g of Corey lactone aldehyde in 75 ml of dimethoxyethane is added dropwise to the mixture; the latter is agitated for one hour at −30° and for 1½ hours at −15°. By adding 11 ml of glacial acetic acid, the reaction is terminated. The mixture is diluted with diethyl ether and neutralized by shaking with saturated sodium bicarbonate solution. The organic phase is washed with saturated sodium chloride solution, dried with magnesium sulfate and, after filtration, concentrated to dryness under vacuum, thus obtaining 11.86 g of the title compound. After purification, the yield is 98.6% of theory.

IR: 1760 $cm^{-1}$ (3-one), 1720 $cm^{-1}$ (7-benzoate), 1700 $cm^{-1}$ (3-oxo)

1b) (1S,5R,6R,7R)-6-[(E)-(3RS,4RS)-3-Hydroxy4-methylnon-1-en-6-ynyl]-7-benzoyloxy-2-oxybicyclo[3.3.0]octan-3-one 11.8 g of crude product of the compound prepared according to (1a) is dissolved in 400 ml of anhydrous methyl alcohol, cooled to −40° and 6.59 g of sodium borohydride is added. After 20 minutes, 11.6 ml of glacial acetic acid is gently added dropwise. The mixture is allowed to warm up to room temperature and then the solvent is removed by evaporation under vacuum at maximally 30°. The residue is combined with methylene chloride. The organic phase is washed respectively once with water, 3% sodium bicarbonate solution, and semisaturated sodium chloride solution. The mixture is dried with magnesium sulfate, filtered, and the filtrate concentrated to dryness under vacuum. The thus-obtained 11.65 g of crude product is chromatographed on silica gel with a pentane-diethyl ether gradient system to separate the 3R- and 3S-isomers. Besides 250 mg of starting compound, 5.04 g of the S-isomer is obtained, corresponding to 51% of theory, and 4.44 g of the R-isomer is obtained =45% of theory. By reoxidation of the R-isomer (Jones reagent in acetone), and repetition of the reaction, the yield of S-isomer can be increased to above 75%.

IR: 3460 $cm^{-1}$ (3-hydroxy), 1760 $cm^{-1}$ (3-one), 1720 $cm^{-1}$ (7-benzoate)

1c) (1S,5R,6R,7R)-6-[(E)-(3S,4RS)-3-Hydroxy-4-methylnon-1-en-6-ynyl]-7-hydroxy-2-oxabicyclo[3.3.0]octan-3-one 7.03 g of the compound according to Example (1b) (S-isomer) is dissolved in 65 ml of anhydrous methyl alcohol; 1.05 g of anhydrous potassium carbonate is added and the mixture stirred under argon and exclusion of moisture for 3 hours at room temperature. Then the mixture is neutralized by adding semiconcentrated hydrochloric acid, and the methyl alcohol is distilled off under vacuum at a bath temperature of maximally 30°. The residue is dissolved in dichloromethane and dried with magnesium sulfate. The residue remaining after removing the drying agent by filtration and elimination of the solvent is purified by chromatography on silica gel with a dichloromethane/acetone system, yielding 4.23 g, corresponding to 81.6% of theory.

IR: 3350 $cm^{-1}$ (dihydroxy), 1760 $cm^{-1}$ (3-one)

1d) (1S,5R,6R,7R)-6-[(E)-(3S,4RS)-4-Methyl-3-methyl3-(tetrahydropyran-2-yloxy)non-1-en-6-ynyl]-(tetrahydropyran-2-yloxy)-2-oxabicyclo[3.3.0]-octan-3-one 2.10 g of the compound prepared according to Example (1c) is dissolved in 65 ml of dried dichloromethane, 1.54 ml of dihydropyran and 10 mg of p-toluenesulfonic acid monohydrate are added to the mixture, and the latter is stirred for 2 hours at room temperature. The reaction solution is washed once each with ice-cold dilute sodium bicarbonate solution and ice-cold sodium chloride solution, dried with magnesium sulfate, and concentrated under vacuum. The residue is purified by chromatography on silica gel with a hexane/ethyl acetate system, thus obtaining 2.96 g of the title compound, corresponding to 89.5% of theory.

IR: 1760 cm$^{-1}$ (3-one), 1295, 870 and 815 cm$^{-1}$ (tetrahydropyranyl ether)

1e) (1S,3RS,5R,6R,7R) 6-[(E)-(3S,4RS)-4-Methyl3-(tetrahydropyran-2-yloxy)non-1-en-6-ynyl]-7-(tetrahydropyran-2-yloxy)-2-oxabicyclo[3.3.0]-octan-3-ol 2.96 g of the compound produced in accordance with Example (1d) is dissolved in 75 ml of absolute toluene. While passing argon over the reaction mixture, the latter is cooled to −70° C. and 11.2 ml of a 20% solution of diisobutyl aluminum hydride in toluene is added dropwise thereto. After 30 minutes, the excess hydride is destroyed by dropwise addition of 0.72 ml of isopropyl alcohol. The cooling bath is then removed, the batch is combined with 5.56 ml of water and stirred until the aluminum compounds can be suctioned off. The mixture is then washed with dichloromethane and the filtrate concentrated to dryness under vacuum. The title compound is obtained in quantitative yield.

IR: 1295 cm$^{-1}$, 870 cm$^{-1}$ and 815 cm$^{-1}$ (tetrahydropyranyl ether), 3400 cm$^{-1}$ (3-ol)

1f) 11,15-Bis(tetrahydropyran-2-yloxy)-16,20-dimethyl-18,18,19,19-tetradehydro-PGF$_{2\alpha}$ At 0°, 92 ml of a 1.25-molar solution of n-butyllithium in hexane is added dropwise to a mixture of 24.2 ml of hexamethyldisilazane and 70 ml of tetrahydrofuran freshly distilled from lithium aluminum hydride. After stirring for 15 minutes, this lithium silazide solution is added dropwise to a suspension of 25.6 g of carboxybutyltriphenylphosphonium bromide in 295 ml of absolute tetrahydrofuran. Once the reaction to the ylide is finished, a solution of 3.15 g of the compound prepared according to Example (1e) in 200 ml of absolute tetrahydrofuran is added thereto and the batch is heated to 40°-45° for 2 hours. Then the mixture is precipitated in ice-cold 10% sodium chloride solution, acidified to pH 4 by adding 10% citric acid solution, and extracted five times with diethyl ether. The combined extracts are then extracted four times with icecold 2.5% strength sodium hydroxide solution. The alkaline extract is acidified with 10% citric acid solution and reextracted five times with diethyl ether. The extract is dried with magnesium sulfate, filtered, and concentrated under vacuum. The residue is processed further in the crude state.

1g) 11,15-Bis(tetrahydropyran-2-yloxy)-16,20-dimethyl)-18,18,19,19-tetradehydro-PGF$_{2\alpha}$Methyl Ester 5.22 g of the crude product obtained according to Example (1f) is dissolved in 125 ml of dichloromethane and cooled to 0°. Then ethereal diazomethane solution is added until a small excess is present; the mixture is allowed to react for another 15 minutes and then the excess is destroyed by a few drops of acetic acid. The residue remaining after removing the solvent by distillation is purified by chromatography on silica gel with a hexane/acetone system, thus obtaining 2.72 g of the methyl ester, i.e. 71.2% of theory, based on the lactol according to Example (1e).

IR: 3450 cm$^{-1}$ (9-OH), 1730 cm$^{-1}$ (methyl ester)

1h) 11,15-Bis(tetrahydropyran-2-yloxy)-16,20-dimethyl)-5-iodo-18,18,19,19-tetradehydro-PGI$_1$ Methyl Ester A solution of 5.89 g of sodium bicarbonate in 85 ml of water is added to a solution of 2.68 g of the methyl ester obtained according to Example (1g) in 60 ml of diethyl ether. The mixture is cooled to 0° under vigorous agitation, and a solution of 2.53 g of iodine in 35 ml of diethyl ether is added dropwise. The mixture is further stirred at 0° for 2 hours. The reaction solution is introduced into a separatory funnel, the phases are separated, and the ether phase is washed once with 5% sodium thiosulfate solution and twice with water. The combined aqueous phases are reextracted with diethyl ether. The organic phase is dried with magnesium sulfate. The residue obtained after filtering off and concentration is purified by chromatography on silica gel with a hexane/acetone system. Yield: 3.13 g, corresponding to 95% of theory.

IR: 1730 cm$^{-1}$ (methyl ester)

1i) 11,15-Bis(tetrahydropyran-2-yloxy)-16,20-dimethyl-18,18,19,19-tetradehydro-PGI$_2$ Methyl Ester 483 mg of the methyl ester obtained according to (1h) is dissolved in 7 ml of anhydrous benzene, combined with 1.54 ml of diazabicycloundecene and stirred under argon for 2.5 hours at 55°-60°. After cooling to room temperature, the mixture is diluted with ethyl acetate and washed three times with water. The aqueous extract is reextracted once with ethyl acetate, and the organic phase is dried with magnesium sulfate. The residue obtained after filtration and evaporation of the solvents is further processed as the crude product.

1j) 7-Oxo-11,15-bis(tetrahydropyran-2-yloxy)16,20-dimethyl-18,18,19,19-tetradehydro-PGI$_2$ Methyl Ester 145 mg of the crude product obtained according to (1i) is dissolved in 5 ml of dioxane. After adding 0.05 ml of hexamethyldisilazane and 41 mg of freshly sublimed selenium dioxide, the mixture is stirred for one hour under argon at 100°, then cooled off to room temperature, and the reaction mixture is poured into alkaline ice water. Then the mixture is extracted alternatingly twice each with diethyl ether and with ethyl acetate, the combined extracts are washed once with water, and the organic phase is dried with magnesium sulfate. Then the mixture is filtered and concentrated to dryness under vacuum. The residue is separated by preparative thin-layer chromatography on silica gel plates in a system of hexane/ethyl acetate/triethylamine (7/3/0.5), thus obtaining 48 mg of crude title compound from which, after another purification in the system of dichloromethane/diethyl ether (85/15), 36 mg of pure product is obtained. Besides the title compound, 45 mg of crude 5-oxo-11,15-bis(tetrahydropyran-2-yloxy)-16,20-dimethyl-6,7-dehydro-18,18,19,19-tetradehydro-PGI$_1$ methyl ester is produced; the yield of title compound, based on the methyl ester according to Example (1h) is 29.8% of theory.

IR: 1730 cm$^{-1}$ (7-oxo and methyl ester), 1650 cm$^{-1}$ (5-ene)

1k) 7-Oxo-16,20-dimethyl-18,18,19,19-tetradehydro-PGI$_2$ Methyl Ester 415 mg of the 7-oxa compound produced according to Example (1j) is combined with 11 ml of a mixture of 65 parts of glacial acetic acid, 35 parts of water and 10 parts of tetrahydrofuran, and the mixture is stirred under argon for 24 hours at room temperature. The main quantity of acetic acid is distilled off under vacuum at room temperature. The remaining acetic acid is removed by distilling twice with toluene. The residue is purified by chromatography on silica gel with a hexane-/acetone system, yielding 246 mg of the title compound, corresponding to 84% of theory.

IR: 3460 cm$^{-1}$ (11,15-diol), 1730 cm$^{-1}$ (methyl ester), 1700 cm$^{-1}$ (shoulder) (7-oxo), 1650 cm$^{-1}$ (5-ene)

11) 7-Oxo-16,20-dimethyl-18,18,19,19-tetradehydro-PGI$_2$ 221 mg of the compound prepared according to (1k) is dissolved in 8 ml of methyl alcohol, 1.55 ml of a solution of 200 mg of potassium hydroxide in 2.5 ml of water is added and the mixture is stirred under argon at room temperature for 20 hours. The methyl alcohol is distilled off under vacuum at room temperature and the residue is taken up in water, extracted three times with diethyl ether, and the aqueous phase is acidified by adding 10% citric acid solution, and again extracted three times with diethyl ether and once with ethyl acetate. The extract is dried with magnesium sulfate, filtered, and freed of the solvents under vacuum. The resultant crude product is purified by preparative thin-layer chromatography in the system dichloromethane/methyl alcohol (8/2), thus obtaining 114 mg of pure 16,20-dimethyl-7-oxo-18,18,19,19-tetradehydro-PGI$_2$, i.e. 53.4% of the theoretical yield.

IR: 3400 cm$^{-1}$ (broad) (11,15-diol+acid-OH), 1710 cm$^{-1}$ (broad) (acid+7-oxo), 1650 cm$^{-1}$ (5-ene)

EXAMPLE 2

16,20-Dimethyl-7-oxo-19,19,20,20-tetradehydro-PGI$_2$ 2a) (1S,5R,6R,7R)-6-[(E)-(4RS)-3-Oxo-4-methyl-1-nonen-7-ynyl]-7-benzoyloxy-2-oxabicyclo-[3.3.0]octan-3-one A solution of 7.56 g of dimethyl-2-oxo-3-methyl-6-octynylphosphate in 60 ml of dimethoxyethane is to a suspension of 1.33 g of sodium hydride (55% strength in oil) in 65 ml of dimethoxyethane at room temperature. Then the solution is agitated for 30 minutes at room temperature and cooled to $-30°$ C. Subsequently, at $-20°$ C., a solution of 7.66 g of (1S,5R,6R,7R)-6-formyl-7-benzoyloxy-2-oxabicyclo[3.3.0]octan-3-one in 84 ml of dimethoxyethane is added thereto and the mixture is stirred for another 2 hours at room temperature. The crude product is isolated analogously to Example (1a), thus obtaining 12.95 g of the title compound as an oil.

IR 1760 cm$^{-1}$, 1720 cm$^{-1}$, 1700 cm$^{31\ 1}$, 1640 cm$^{-1}$, 1460 cm$^{-1}$ 2b) (1S,5R,6R,7R)-6-[(E)-(3S,4RS)-3-Hydroxy-4-methyl-1-nonen-7-ynyl]-7-hydroxy-2-oxabicyclo[3.3.-0]octan-3-one Analogously to Examples (1b)–(1c), 4.82 g of the title compound is obtained, starting with 12.88 g of the ketone produced in Example (2a).

IR: 3600, 2965, 1770, 975 cm$^{-1}$ 2c) 16,20-Dimethyl-7-oxo-19,19,20,20-tetradehydro-PGI$_2$ Analogously to Examples (1d)–(11), 143 mg of the title compound is obtained, starting with 4.70 g of the diol produced in Example (2b).

IR: 3400 (broad), 1710, 1650, 1460, 1360 cm$^{-1}$

EXAMPLE 3

16,20-Dimethyl-7-oxo-18,19-didehydro-PGI$_2$ 3a) (1S,5R.6R.7R)-6-[(1E,6Z)-(3S,4RS)-3-Hydroxy-4-methyl-1,6-nonadienyl]-7-hydroxy-2-oxabicyclo[3.3.-0]octan-3-one A solution of 5.20 g of the acetylene compound prepared according to Example (1c) in 170 ml of tetrahydrofuran is combined with 1.7 g of Lindlar catalyst and stirred for 60 minutes under a hydrogen atmosphere (normal pressure). After this hour, the hydrogen absorption is complete, and the suspension is separated from the catalyst by filtration. The filtrate is concentrated to dryness under vacuum, thus obtaining 5.22 g of the title compound.

IR: 3350, 1760 cm$^{-1}$

3b). 16,20-Dimethyl-7-oxo-18,19-didehydro-PGI$_2$

Analogously to Examples (1d)–(11), 171 mg of the title compound is obtained, starting with 5.10 g of the diol prepared in Example (3a).

IR: 3400 (broad), 1710, 1650, 1460, 1360 cm$^{-1}$

EXAMPLE 4

16,20-Dimethyl-7-oxo-19,20-didehydro-PGI$_2$

In analogy to Examples (3a)–(3b), 160 mg of the title compound is produced, starting with 4.82 g of the diol obtained according to Example (2b).

IR: 3400 (broad), 1710, 1640, 1350 cm$^{-1}$

We claim:

1. A 20-alkyl-7-oxoprostacyclin derivative of formula I

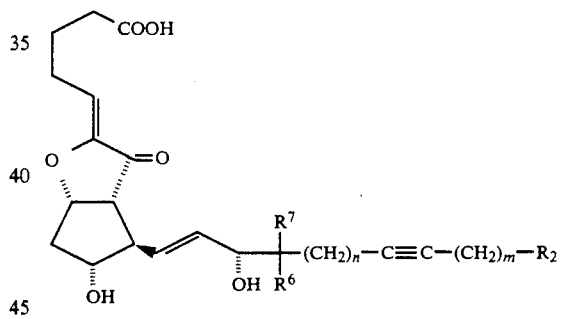

wherein
n is 1;
R$_2$ is a straight-chain or branched-chain C$_{1-4}$-alkyl group;
m is 1; and
R$_6$ and R$_7$ each independently are H or a straight-chain or branched-chain C$_{1-4}$-alkyl group;
or a salt thereof with a physiologically compatible base.

2. A compound of claim 1, which is 16,20-dimethyl-7-oxo-18,18,19,19-tetradehydro-PGI$_2$.

3. A pharmaceutical preparation comprising an effective amount of a compound of claim 1 and a pharmaceutically acceptable excipient.

4. A method of treating hypertension, comprising administering an effective amount of a compound of claim 1.

5. A method of inhibiting thrombocyte aggregation, comprising administering an effective amount of a compound of claim 1.

* * * * *